United States Patent [19]

Kortum

[11] 4,365,632

[45] Dec. 28, 1982

[54] METHOD AND APPARATUS FOR INDUCING IMMUNOLOGICAL AND RESISTANT RESPONSE IN MAMMARY GLANDS

[76] Inventor: William M. Kortum, 180 Ely Rd., Petaluma, Calif. 94952

[21] Appl. No.: 102,795

[22] Filed: Dec. 12, 1979

Related U.S. Application Data

[63] Continuation-in-part of Ser. No. 903,343, May 5, 1978, Pat. No. 4,202,329.

[51] Int. Cl.$^{3}$ .............................................. A61B 17/00

[52] U.S. Cl. ............................... 128/303 R; 128/1 R; 128/130

[58] Field of Search ............... 128/130, 247, 1 R, 260, 128/303 R; 119/1

[56] References Cited

U.S. PATENT DOCUMENTS

| | | | |
|---|---|---|---|
| 2,626,807 | 1/1953 | Carlton | 273/417 |
| 2,734,746 | 2/1956 | Sametz et al. | 273/417 |
| 3,089,704 | 5/1963 | Wolf | 273/417 |
| 3,253,590 | 5/1966 | Birnberg et al. | 128/130 |
| 3,590,816 | 7/1971 | Rosenthal | 128/130 |
| 3,805,767 | 4/1974 | Erb | 128/130 |
| 3,858,571 | 1/1975 | Rudolph | 128/130 |
| 3,905,360 | 9/1975 | Zaffaroni | 128/130 |
| 4,133,533 | 1/1979 | Doyle | 273/417 |

FOREIGN PATENT DOCUMENTS

| | | | |
|---|---|---|---|
| 887172 | 1/1962 | United Kingdom | 273/417 |
| 1441110 | 6/1976 | United Kingdom | 273/417 |
| 1505470 | 3/1978 | United Kingdom | 273/417 |

*Primary Examiner*—Richard J. Apley
*Assistant Examiner*—T. J. Wallen
*Attorney, Agent, or Firm*—Bertram I. Rowland

[57] ABSTRACT

Process and apparatus are provided for stimulating immune resistance by the introduction of at least one relatively small solid non-toxic substantially non-biodegradable body, having non-specific antigenic action, into each gland cistern of the udder. The body is sufficiently flexible or elastic and of a shape so as to be capable of being shaped into a form small enough to be inserted into the gland cistern through the lactiferous duct and then reformed to its original shape which inhibits its passage from the gland cistern into the teat cistern. The continued presence of the non-specific antigenic body induces immune resistance including an increase in the number and activity of phagocytic cells, particularly leukocyte cells, in the udder. The continued presence of these increased numbers of activated phagocytic cells provides protection against bacterial invasion through the streak canal without degrading milk quality.

10 Claims, 17 Drawing Figures

METHOD AND APPARATUS FOR INDUCING IMMUNOLOGICAL AND RESISTANT RESPONSE IN MAMMARY GLANDS

BACKGROUND OF THE INVENTION

This application is a continuation-in-part of copending application Ser. No. 903,343, filed May 5, 1978, now U.S. Pat. No. 4,202,329.

1. Field of the Invention

Of particular concern in dairy herds is inflammation of the mammary gland referred to as mastitis. Mastitis results in inflammation, which in acute mastitis results in swelling, redness, heat, pain and loss of function. The majority of occurrences of mastitis are bacterial in origin.

The use of antibiotics has been highly successful in curing and reducing the incidence of mastitis. However, the use of antibiotics has many disadvantages. While antibiotics have been capable of controlling the incidence of mastitis results from Staphylococci and Streptococci infection, the result has been that the effectiveness of the natural protective resistance to other bacterial organisms such as coliform has been diminished. That is, apparently when the immunological system of resistance was stressed by either Staphylococci or Streptococci, this system was able to counteract invasion from other organisms. When antibiotics are employed which destroy the aforementioned organisms, the mammary gland becomes susceptible to infection from other organisms which are antibiotic resistant.

It is therefore desirable to find ways to induce this immunological and resistance system to protect the host from bacterial invasion.

2. Brief Description of the Prior Art

Sagiroglu, N., *Proceedings of the Third International Conference on Intrauterine Contraception,* 465–468 (1975) suggests the production of macrophages as a result of introduction of an intrauterine foreign body. Jensen and Eberhart, Am. J. Vet. Res. 36, 619 (1975 teach that vacuolated mononuclear cells found in milk during lactation may be macrophages. Alexander *Annual Review of Medicine* 27:207–224 (1976) teaches that a synthetic pyran copolymer initiates production and activation of macrophages by stimulating the reticuloendothelial system.

SUMMARY OF THE INVENTION

Process and apparatus are provided for enhancing immune resistance, including increasing the natural production of phagocytic cells, including macrophages, in mammary glands. The apparatus employed is a non-toxic body or non-specific antigenic device of a rigid solid, usually having moderate elasticity. The device may be formed so it can be temporarily constrained to a shape in which it can be inserted through the lactiferous duct and past the shelf between the teat and gland cisterns. Upon release of the constraint, the device reforms to a size and shape which inhibits the passage of the device from the gland cistern into the teat cistern, except by exogenous mechanical means. The device remains in the gland cistern until mechanically removed, where during its residence it continuously stimulates leukocyte formation.

The device may be a rod or assume various other shapes, such as coils, rings, discs or the like, which may be folded or extended, so as to be able to pass through the lactiferous duct. The device is provided in aseptic condition, packaged in an aseptic container to inhibit the introduction of undesirable organisms when the device is introduced into the gland cistern.

The device may be of any material having the desired biological and physical characteristics and its antigenicity may be further enhanced by using organic polymers which provide enhanced stimulating activity or by incorporating with the device materials which stimulate immunological activity, e.g., protein antigens.

BRIEF DESCRIPTION OF THE DRAWINGS

FIG. 3 is a side elevational view of a device according to this invention in combination with an insertion device;

FIGS. 4, 5, 6, 7, 8, 9 and 10 are plan views of alternate embodiments of devices according to this invention;

FIGS. 4*a*, 5*a*, 6*a*, 7*a*, 8*a*, 9*a* and 10*a* are diagrammatic views of the devices of FIGS. 4, 5, and 7 to 10 as formed for insertion into an insertion device, a portion of which is depicted.

DESCRIPTION OF THE SPECIFIC EMBODIMENTS

Figure 1:
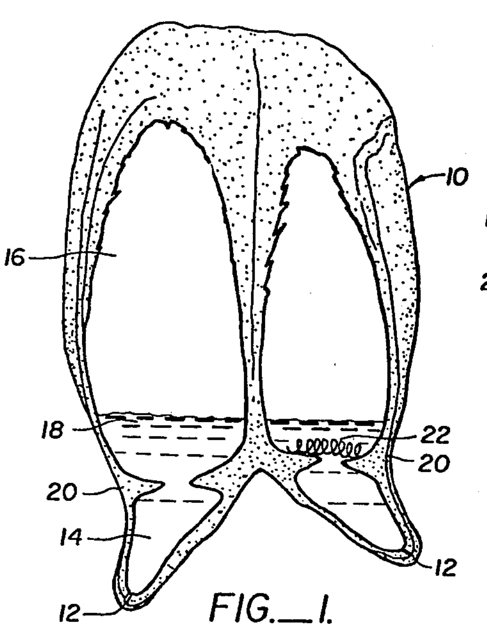
FIG. 1 is a diagrammatic cross-sectional view of the mammary gland having a device according to this invention in one of the gland cisterns.

A process and apparatus are provided in accordance with this invention for stimulating naturally occurring resistance systems and immunological defenses in mammary glands. The methods and apparatii find particular application with the mammary glands of milk-supplying domestic animals, such as cows (bovine), goats (caprine), and the like. The method employs a device or body which is shaped so as to be capable of being inserted through the lactiferous duct past the shelf between the teat and gland cistern and is of such a size and shape, that once inserted in the gland cistern it is generally precluded from entering the teat cistern without external manipulation.

Various shapes or forms of the device may be employed. The simplest form is a small rod which may be inserted through the lactiferous duct and will then float in the gland cistern. The length of the rod will inhibit its moving down into the teat cistern. Alternatively, forms can be employed which may be constrained into a shape which allows them to be introduced through the lactiferous duct. Upon release from the constraint, the device will reform its original shape, expanding to a size which inhibits its passage beneath the shelf between the teat and gland cistern.

These shapes include rods, discs, coils, rings, spirals, hubs with extended spokes, with or without a circumferential ring, and the like. By employing moderately elastic rigid materials, the form may be rolled up or extended to a size where it may be introduced into the gland cistern through the lactiferous duct and teat cistern into the gland cistern, where it will reform into its original form and size and be prevented from passing beyond the shelf between the two cisterns.

Various materials may be used, which for the most part will be organic polymers, either addition or condensation polymers. Conveniently, polyolefins of from 2 to 6, more usually of from 2 to 3 carbon atoms, including copolymers thereof, may be employed, which are either atactic or tactic. Illustrative polymers include polyethylene, polypropylene, ethylene-propylene copolymers and the like. The condensation polymers which may be employed include polyamides, polyurethanes, polyethers, polyesters, and the like. Illustrative polymers include nylon, pyran polymers, etc.

The materials which are employed should be relatively rigid, normally having sufficient elasticity to allow for folding or extension and returning to the original shape and will generally have a density less than 1. The materials will also be non-toxic and preferably non-biodegradable. In addition, different materials may be used, depending on the degree of stimulation of macrophage production which is desired. To enhance immunological stimulation, the device may incorporate antigenic materials, such as protein.

The constraints on the device size are that it be capable of being introduced through the teat sphincter and reside above the teat rosette. Therefore, the device should have a long dimension of greater than about 0.5 cm, preferably greater than about 1.0 cm and not greater than about 2.5 cm, preferably not greater than about 2 cm. In addition, where the device is to be constrained during insertion through the teat sphincter, the device should have a maximum cross section of from about 0.1 cm and not greater than about 0.8 cm, more usually not greater than about 0.5 cm. The significant factor is the ability to insert the device into the gland cistern without injury to the teat, and be of a shape once introduced into the gland cistern as to inhibit its movement into the teat cistern.

Where rods are involved, the rods may be either hollow or solid and, as indicated previously, may assume a variety of shapes. Where discs are involved, they may be continuous sheets or have substantial portions of the sheets removed, preferably the latter.

Conveniently, the device will be inserted under substantially aseptic conditions through the teat sphincter by means of an insertion device. The insertion device will usually be a tube, a rod, or a combination of the two. The particular manner of insertion will depend upon the nature of the device.

In the simplest situation, where a rod, either hollow or solid, is to be employed as the device, a tube may be inserted into the lactiferous duct and extended into the gland cistern. The rod may then be passed through the tube, using an insertion rod to push the device up into the gland cistern.

Where a circular device is employed, such as a coil, spiral, ring, or split ring, the device may be either hollow or solid. In inserting the device, where the device is solid or hollow, having its end either closed or open, the device may be extended by pushing the device through a rigid tube, having an inner diameter, somewhat greater then the outer diameter or cross-section of the rod or ribbon which forms the device, and in the case of a closed ring, about twice the cross-section. The insertion tube is introduced through the teat sphincter and extends up into the gland cistern. The pre-loaded device or body is then pushed through the tube while being expanded or uncoiled until the device extends past the opening of the insertion tube into the gland cistern, where it begins to recover its original form and completely expand or coil. A rod is used to push the device through the tube and into the gland cistern. The insertion tube and rod may then be retracted.

A third alternative is to have a flat object, conveniently round such as a disc, which can be a flat sheet, or a sheet with a plurality of openings, or a hub with extending spokes, with or without a circumferential ring. The sheet must be thin enough so as to be conveniently rolled to form a roll of sufficiently small diameter to be capable of passing through an insertion tube. With the hub and spokes, the spokes may be brought together, so as to be substantially parallel and introduced into the insertion tube. An insertion rod may then be used to push the device through the insertion tube and into the gland cistern. The most distant points in the disc or other substantially circular device will usually be not more than 3 cm, usually not more than 1.5 cm and be at least 0.5 cm.

In each instance, by employment of an appropriate material, the device will reform to its original shape, so as to be substantially inhibited from entering into the teat cistern.

Alternatively, hollow tubes can be employed having none or one closed end and the tube pulled onto a solid rod having an outer diameter about equal to or slightly less than the inner diameter of the device tube. With the various circular devices, e.g. coil or spiral, the device will be extended into a substantially straight line or moderately curved line onto the rod. The device in its extended form on the insertion rod may now be introduced into the gland cistern through the teat sphincter, so that the device extends into the gland cistern. The rod may now be retracted, while holding the device to prevent its retraction from the gland cistern, until the insertion rod is completely removed, whereby the device will recover its original form and be positioned above the shelf between the cisterns.

For further understanding of the invention, the drawings will now be considered.

In FIG. 1, a cross-section of the mammary gland 10 is depicted having lactiferous duct 12 teat cistern 14 and gland cistern 16 separated by shelf 20. Residing in the gland cistern is device 22, depicted as a coil.

Figure 2:
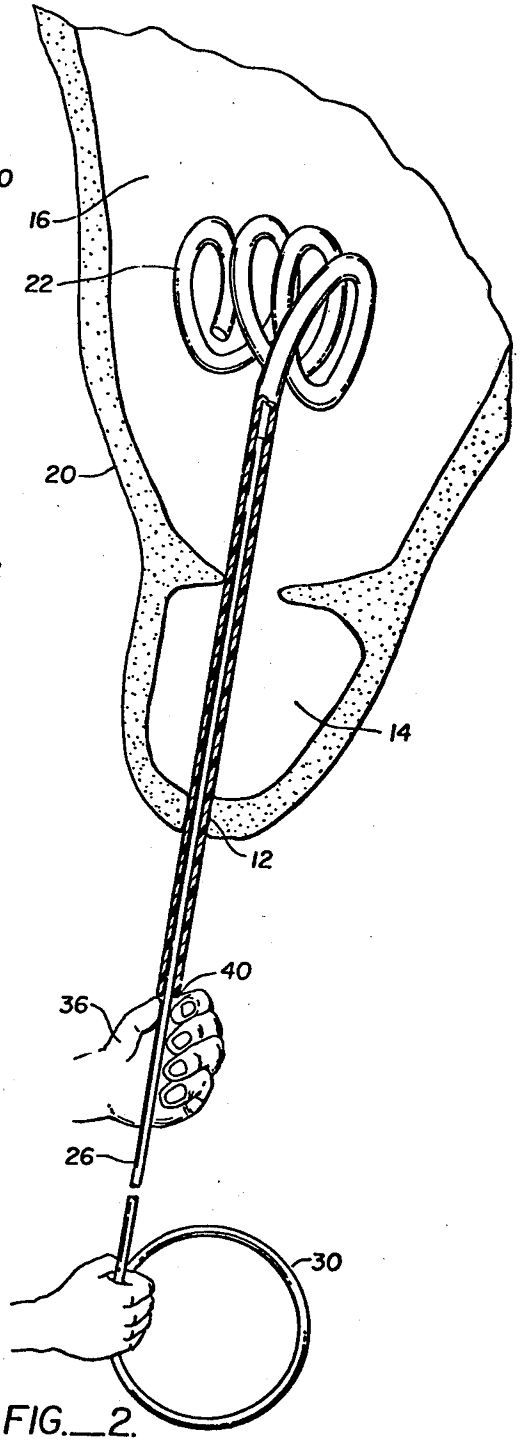
FIG. 2 is a diagrammatic view of the device according to this invention being inserted into the gland cistern.
Figures 3, 5A, 6, 7, 7A, 8, 8A, 9, 10, 10A:
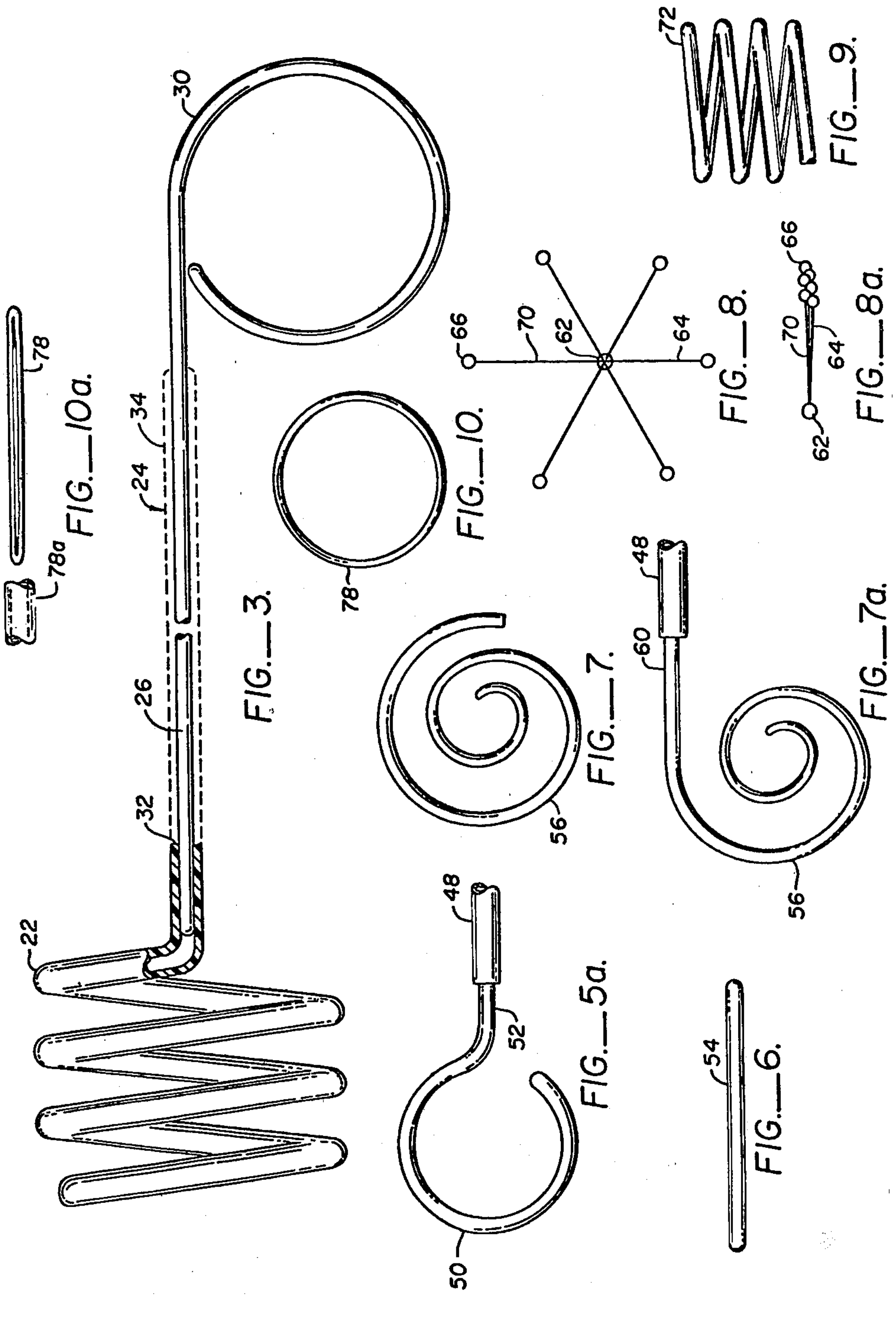

In FIGS. 2 and 3, the manner of inserting a coil device into the gland cistern is shown. The coil device 22 is a hollow tube which is mouned onto insertion configuration 24. The insertion device has a long straight rigid wire 26 ending in a circular handle 30 to provide for convenience of holding and handling. The wire 26 is inserted into the opening 32 of the coiled tube device 22 and the coiled tube device 22 pulled down on the wire so as to be extended into a straight line as depicted by broken line 34.

The insertion configuration 24 with the coil 22 mounted on wire 26 is then passed through the lactiferous duct 12 into the gland cistern 16 by placing fingers 36 at the end 40 of the device 22 nearest the handle 30. By slowly retracting the wire 26, the device 22 will move off of wire 26 and begin to recoil. This is continued until the wire 26 is completely retracted and a major portion of the device 22 is coiled and situated above the shelf 20. The remaining portion of the device 22 situated in the teat sphincter will then be pulled upwards in coiling into the gland cistern. Device 22 will rest on shelf 20 submerged in the milk 18.

When the device is to be removed, it may be manually manipulated by forceps to force its passage past the shelf 20 and the lactiferous duct.

Figure 4:
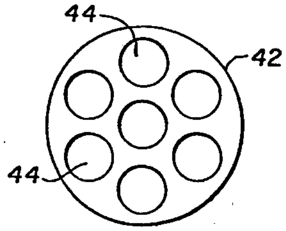
Figure 4A:
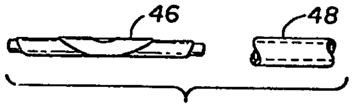

Turning now to FIGS. 4 to 9, a number of different exemplary embodiments of the synthetic antigen device are depicted. They are shown in their original form, as well as in the form in which they would be introduced into the gland cistern by means of an external tube 48 that would contain the device during insertion. The device is expelled from the tube by means of a rod similar to 26. In FIG. 4, a disc device 42 is depicted having a plurality of holes 44 symmetrically situated in the disc. The thickness of the disc will generally be under 3 mm., usually under 2 mm., and may be as thin as 5 mils. The holes 44 add some flexibility to the disc to ease the rolling up of the disc into a roll 46 as depicted in 4*a*. The roll 46 may then be inserted into a tube 48, a portion of which is depicted in FIG. 4*a*. Using a rod, the furled disc 46 may be pushed through tube 48. This mode of insertion may be used with most devices of this invention.

Figure 5:
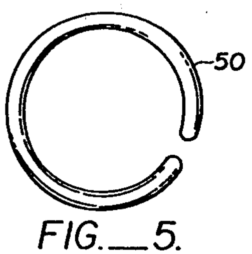

An alternative embodiment is depicted in FIG. 5 as a split ring 50, which may either be solid or hollow. While the split ring is depicted as having sealed ends, the ends may be sealed or unsealed. As shown in FIG. 5*a*, the split ring 50 has sufficient flexibility so that it may be straightened out to form a straight rod 52 and pushed through an insertion tube 48. Using a rod as indicated previously, the split ring can then be forced through the insertion tube 48 into the gland cistern, where it will resume its split ring form 50.

Another embodiment is a straight rod 54 as depicted in FIG. 6. The rod would be of sufficient length so as to prevent its re-entry into the teat cistern and of sufficient buoyancy, so as to float in the milk. When the gland cistern was evacuated, the rod would rest on the shelf 20 until a new supply of milk was formed in the gland cistern 16. The rod will normally be at least 1 cm long, usually from 2 to 4 cm long. In FIGS. 7 and 7*a*, a spiral device 56 with a portion 60 being straightened for introduction into the end of an insertion tube 48 is depicted.

In FIGS. 8 and 8*a*, a device 70 is depicted having a hub 62 and a plurality of spokes 64 terminating in tiny spheres 66. The device may be referred to as a spider. As depicted in FIG. 8*a*, the spokes 64 are bent into substantially parallel positions to compress the device 70, with the spokes radiating in substantially the same direction so as to be easily insertable into a device insertion tube. The spokes may be of the same or different lengths. The spider 70 in its compressed form may be introduced into an insertion tube and employing a rod may be pushed through the insertion tube into the gland cistern.

A coil 72 is depicted in FIG. 9 which is shown as having open ends. However, a coil device may be either solid or hollow, and may have one or both ends open or closed. As indicated previously, the coil has sufficient flexibility that it may be straightened out by being forced into an insertion device tube and then pushed through the tube into the gland cistern or fitted onto a stiff rod and inserted into the gland cistern.

Finally, an "O" ring 78 is depicted in FIG. 10, having specifications similar to those of split ring 50 although made of smaller diameter tubing. FIG. 10*a* shows the ring 78 collapsed into a substantially linear form and fitted into insertion device 48.

Figure 11:
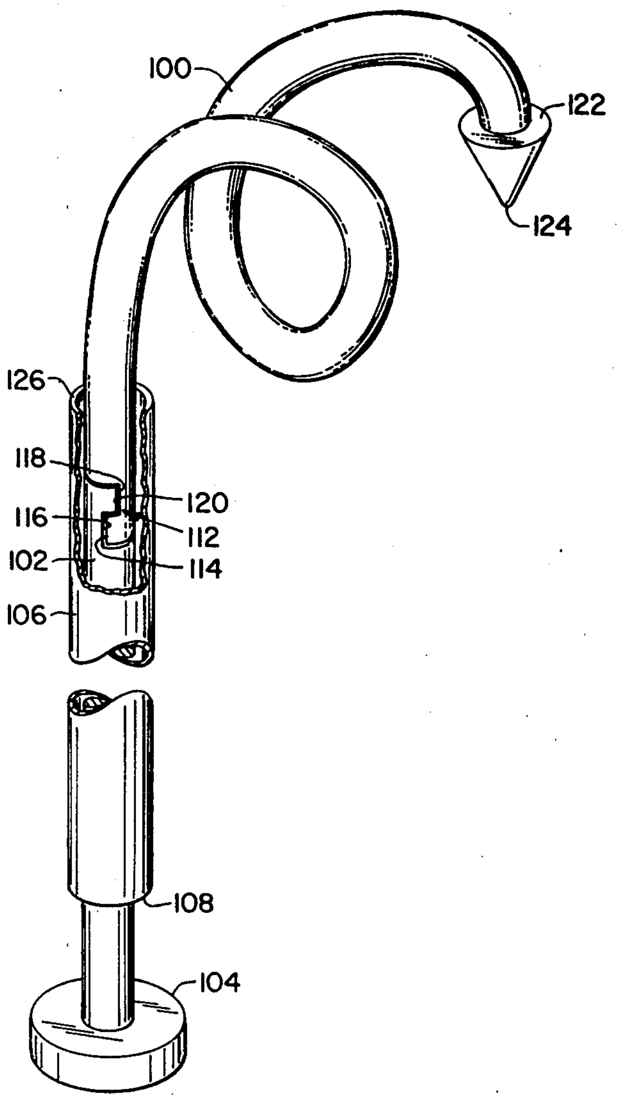
FIG. 11 is a side cross-sectional view in partial cutaway of a further embodiment.

Referring to FIG. 11, a further alternative embodiment of the IMD is shown. In order to preserve the coiled substantially elastic plastic tube 100 in its tightest helix such that it does not lose its architectural memory, it is desired to store it in an unstraightened state. However, it is recommended that it also be maintained in an aseptic condition until insertion. To this end an insertion mechanism is provided which does not require direct handling of the coiled tube device 100. The insertion mechanism comprises a plunger rod 102 disposed within a straight rigid inserting cannula 106. The rod has at one end a plunger handle 104 and at the other end a clasp 112 which attaches with an overlapping end of the coiled tube 100. The clasp 112 is operative to release the end of the coiled tube 100 whenever the clasp 112 is urged beyond the opening 126 of the cannula 106. Mere lateral displacement of the rod 102 from the tube 100 effects release.

Many configurations of the clasp 112 are suggested. A specific configuration comprises a shoulder 114 in the tube 100 which mates with a lateral keyway 116 in the rod 102 and an adjacent shoulder 118 in the rod 102 which mates with a lateral keyway 120 in the coil 100. The shoulders 114 and 118 are laterally recessed so that the connected rod 102 and coil 100 present a uniform diameter to the interior of the cannula 106.

In operation the handle 104 is pulled to temporarily draw the coiled tube 100 into the cannula 106, thus briefly straightening the tube 100. The tube 100 may be drawn until the shoulder 122 of its blunt tip 124 rests against the end 126 of the cannula 106. The cannula may be removed from its aseptic container (not shown) such as a bag. The cannula is then inserted into the teat sphincter with the blunt tip 124 leading the penetration. Thereafter the plunger rod 102 is collapsed so the handle 104 abuts to the second end 108. The clasp 112 is thus extended beyond the first cannula end 126, thus releasing the tube 100 in a coiled state within the gland cistern. The cannula is then withdrawn.

This embodiment allows sterile insertion of the tube 100 without causing the tube 100 to be stretched for a time sufficient to seriously lose its architectural memory of its coiled condition.

The presence of the various devices in the gland cistern, has the effect of being a non-specific synthetic antigen that can stimulate an increase and activation of phagocytic cells, particularly leukocytes, in the gland cistern, to protect the udder from bacterial invasion resulting in disease and inflammation, particularly mastitis. The device employed will not interfere with the normal milking of the cow and will remain effective throughout the period of lactation and subsequent lactations. Due to its flexibility, the device may be withdrawn mechanically without the aid of an insertion device. During lactation, between milkings, the device will be in intermittent contact with the gland cistern and when the milk is removed during milking the device will be retained by the shelf between the gland cistern and the teat cistern.

The increase and activation of phagocytic cells is limited to the area of the gland cistern, acting as a barrier to the migration of infective agents into the alveoli where milk is produced. Leukocyte cell production is diluted in the total milk production of the gland and therefore milk quality is not degraded.

In order to demonstrate the subject invention, the following study was carried out. A cow was chosen having CMT(California Mastitis Test) negative readings on the right front and left rear quarters. An alcohol scrub was made on the right front teat. A $\frac{5}{8}$ths inch long 1/6th inch O.D. polyethylene tubing coil of 5 turns was placed in the gland cistern above the teat cistern as follows. Employing a 1 mm. wire rod upon which the coil was pulled, the rod with the coil mounted on it was introduced through the teat sphincter into the gland cistern. The rod was then retracted while the coil was pushed upward until all of it was in the gland cistern. A CMT No. 1 (500,000–800,000 cells/ml.) was observed 24 hours post implacement in the deviced quarter. A bacterial culture of milk from the deviced quarter was negative on the 8th day. In addition, the milk had a somatic cell ratio containing about 50 percent polymorphonuclear leukocytes.

A coliform culture used for challenging bovine mammary glands, obtained from the U.C. Davis School of Veterinary Medicine was diluted to 8,000 organisms/ml. This culture (0.5 ml) was infused into the deviced quarter on the 8th day. The same amount of culture was infused into the CMT negative left rear quarter. An 8 hour sample showed CMT No. 1 in both challenged quarters. At 24 hours, the formerly negative left rear quarter was hot, swollen, had flakes in the milk and was CMT No. 3. The deviced quarter remained CMT No. 1 and demonstrated no clinical signs of swelling, heat or abnormal milk.

The conclusions drawn from the study were that the right front quarter had been stimulated to an adequate leukocyte level to phagocytize the innoculated organisms, before they could multiply into a clinically mastitis quarter. By contrast, the non-deviced left rear quarter did not have a macrophage or leukocyte level sufficient to overcome the challenge.

It is evident from the above results that the subject method and apparatus provide for a method of protecting the udders of milk producing animals from bacterial invasion. The method is simple, it is readily administered to the animal, and can remain in the animal for long periods of time, to provide the desired protection against bacterial invasion. Furthermore, the process and device do not cause a degradation of milk quality.

Conveniently, the devices can be supplied to an aseptic condition by having one or more devices enclosed in an hermetically sealed pouch or container which maintains the device in its aseptic condition until ready for use. Included in the same pouch or container or a separate pouch or container will be the insertion device, which is also aseptic. Depending upon the nature of the device to be introduced into the gland cistern, the insertion device may be either a rod or a tube with plunger. Normally, the outer diameter of the tube will not exceed 8 mm., more usually, not exceed 5 mm., so that it can be conveniently inserted through the teat sphincter. The insertion rod, where a hollow device is employed, will normally not exceed 3 mm. outer diameter, more usually not exceed 2 mm. outer diameter, and preferably be from about 0.5 to 2 mm. outer diameter. Conveniently, the insertion devices may be included with the antigenic device in the same aseptic container.

In accordance with the subject invention, devices are provided which are employed in a method for protecting milk producing animals from bacterial infection in the udder e.g. mastitis. The devices are lightweight, non-toxic bodies of a density (including air space) about equal to that of milk, so they will float in the milk when present in the udder. The material employed, with the devices which must be extended when introduced through the teat sphincter, need only be sufficiently elastic to allow for extension during its introduction and have sufficient memory to reform into its original shape after introduction. The presence of the device in the gland cistern making intermittent tissue contact stimulates immune resistance with the production of phagocytic cells so as to protect against bacterial invasion in the teat and gland cistern.

Although the foregoing invention has been described in some detail by way of illustration and example for purposes of clarity of understanding, it will be obvious that certain changes and modifications may be practiced within the scope of the appended claims.

What is claimed is:

1. A kit inhibiting bacterial infection in an udder of a milk-producing domestic animal comprising:

a plastic non-toxic antigenic device comprising an elongate cylinder having at least one end tapered so that said end may be inserted into the udder through the teat sphincter and be retained in the gland cistern;

means comprising a straight hollow tube for introducing said device into the udder; and means comprising a rod disposed within said tube for inserting said device into the gland cistern;

said device having an appendage capable of being drawn into said tube; and said inserting means having at one end of said rod a clasp means for attaching to said device appendage, said clasp means being operative to hold said device appendage whenever said one end is within said tube and to release said device appendage whenever one end is external said tube.

2. A kit according to claim 1 wherein said elongate cylinder assumes an unstraightened shape when in an unstressed state and wherein at least a portion of said cylinder is capable of being drawn in straightened form into said tube by said rod.

3. A kit according to claim 2 wherein said device includes a clasp means for mating with said rod clasp means, said device clasp means being located at the end of the cylinder opposite to the tapered end and wherein said device clasp means is capable of being separated from said rod clasp means only by lateral movement and wherein said tube is of a sufficiently small inner diameter to prevent clasp separation by lateral movement whenever said rod clasp means and said device clasp means are mated within said tube.

4. A kit according to claim 3 wherein the tapered end of the elongate cylinder comprises a blunted point having a shoulder which limits the extent which the device can be drawn into said tube and wherein said tube and said blunted point cooperate for introducing said device into the udder.

5. A kit according to claim 4 wherein said device in an unstressed state is a coil.

6. A kit according to claim 4 wherein said device in an unstressed state is a spiral.

7. A kit according to claim 4 further including an aseptic container of sufficient size to enclose said device in its unstraightened state together with said inserting means and said introducing means.

8. A system comprising an antigenic device and an apparatus for inserting said device through a teat sphincter and into the udder of a domestic milk-producing animal, wherein:

(a) the antigenic device is a nonlinear resilient tube capable of being substantially straightened and having a clasp at one end and a means for penetrating the teat sphincter at the other end; and (b) the apparatus includes:

a hollow tube having an internal diameter substantially equal to the diameter of the tube but insufficient to allow entry of the means for penetrating; and means for engaging the clasp and drawing the device into the tube until only the means for penetrating projects out of the tube.

9. A system as in claim 8, wherein the means for penetrating is a blunt conical tip having a shoulder which projects radially outward from the tube and prevents the tip from being drawn into the tube.

10. A system as in claim 8, wherein the maximum cross-sectional dimension of the device is in the range from 0.1 to 0.8 cm.

* * * * *